(12) United States Patent
Kudo et al.

(10) Patent No.: US 9,622,921 B2
(45) Date of Patent: Apr. 18, 2017

(54) ABSORBENT ARTICLE WITH TOPSHEET, TOP-LAYER SHEET AND COMPRESSING PORTIONS

(75) Inventors: Jun Kudo, Kagawa (JP); Yuji Takahashi, Kagawa (JP); Mari Yasui, Kagawa (JP)

(73) Assignee: Unicharm Corporation, Ehime (JP)

( * ) Notice: Subject to any disclaimer, the term of this patent is extended or adjusted under 35 U.S.C. 154(b) by 343 days.

(21) Appl. No.: 14/118,730

(22) PCT Filed: May 15, 2012

(86) PCT No.: PCT/JP2012/062344
§ 371 (c)(1),
(2), (4) Date: Jan. 23, 2014

(87) PCT Pub. No.: WO2012/161023
PCT Pub. Date: Nov. 29, 2012

(65) Prior Publication Data
US 2014/0163507 A1    Jun. 12, 2014

(30) Foreign Application Priority Data
May 20, 2011  (JP) ................. 2011-113832

(51) Int. Cl.
*A61F 13/47* (2006.01)
*A61F 13/511* (2006.01)
(Continued)

(52) U.S. Cl.
CPC .... *A61F 13/51311* (2013.01); *A61F 13/4756* (2013.01); *A61F 13/5116* (2013.01); *A61F 13/51104* (2013.01)

(58) Field of Classification Search
CPC ............ A61F 13/4756; A61F 13/51104; A61F 13/5116; A61F 13/51108
(Continued)

(56) References Cited

U.S. PATENT DOCUMENTS

| 5,913,850 A * | 6/1999 | D'Alessio et al. ........... 604/378 |
| 2005/0148971 A1 * | 7/2005 | Kuroda et al. ................ 604/380 |

(Continued)

FOREIGN PATENT DOCUMENTS

| CN | 1868429 A | 11/2006 |
| CN | 101410080 A | 4/2009 |

(Continued)

OTHER PUBLICATIONS

Chinese Office Action and English translation from corresponding Chinese application No. 201280024486.1 dated Aug. 21, 2014 (13 pgs).

(Continued)

*Primary Examiner* — Kathryn E Ditmer
(74) *Attorney, Agent, or Firm* — Brinks Gilson & Lione

(57) ABSTRACT

An absorbent article that has a topsheet, a backsheet, and an absorber, and a liquid-permeable top-layer sheet is joined with a skin contact surface side of the topsheet. The top-layer sheet is arranged along a lengthwise direction in a central portion of a widthwise direction of the absorbent article, and non-joined regions that are not joined with the topsheet are provided at both widthwise ends of the top-layer sheet. A compressing portion in which at least the topsheet and the absorber are compressed in the thickness-wise direction, is formed around the non-joined region.

20 Claims, 8 Drawing Sheets

(51) Int. Cl.
*A61F 13/513* (2006.01)
*A61F 13/475* (2006.01)

(58) Field of Classification Search
USPC .......................................................... 604/380
See application file for complete search history.

(56) References Cited

U.S. PATENT DOCUMENTS

| | | | | |
|---|---|---|---|---|
| 2006/0271008 | A1* | 11/2006 | Tanio | A61F 13/47263 604/385.31 |
| 2010/0280475 | A1* | 11/2010 | Kudo | A61F 13/47218 604/380 |
| 2011/0319851 | A1* | 12/2011 | Kudo | A61F 13/4704 604/380 |
| 2012/0095425 | A1* | 4/2012 | Nishitani | A61F 13/47218 604/380 |

FOREIGN PATENT DOCUMENTS

| | | |
|---|---|---|
| CN | 101541277 A | 9/2009 |
| JP | 2003-286642 A | 10/2003 |
| JP | 2006-014880 | 1/2006 |
| JP | 2006-181294 | 7/2006 |
| JP | 2008-326092 | 12/2006 |
| JP | 2008-132084 | 6/2008 |
| JP | 2009-207684 | 9/2009 |
| JP | 2010-148708 A | 7/2010 |
| JP | WO 2010074339 A1 * | 7/2010 ......... A61F 13/4704 |
| JP | WO 2010117015 A1 * | 10/2010 ......... A61F 13/4704 |

OTHER PUBLICATIONS

International Search Report from corresponding PCT application No. PCT/JP2012/062344 dated Jul. 24, 2012 (4 pgs).

Japanese Office Action from corresponding Japanese application No. JP 2011-113832 dated Nov. 19, 2014 (6 pgs).

Taiwanese Examination Result and English translation from corresponding Taiwanese application No. 101117829 dated Jul. 31, 2015 (9 pgs).

* cited by examiner

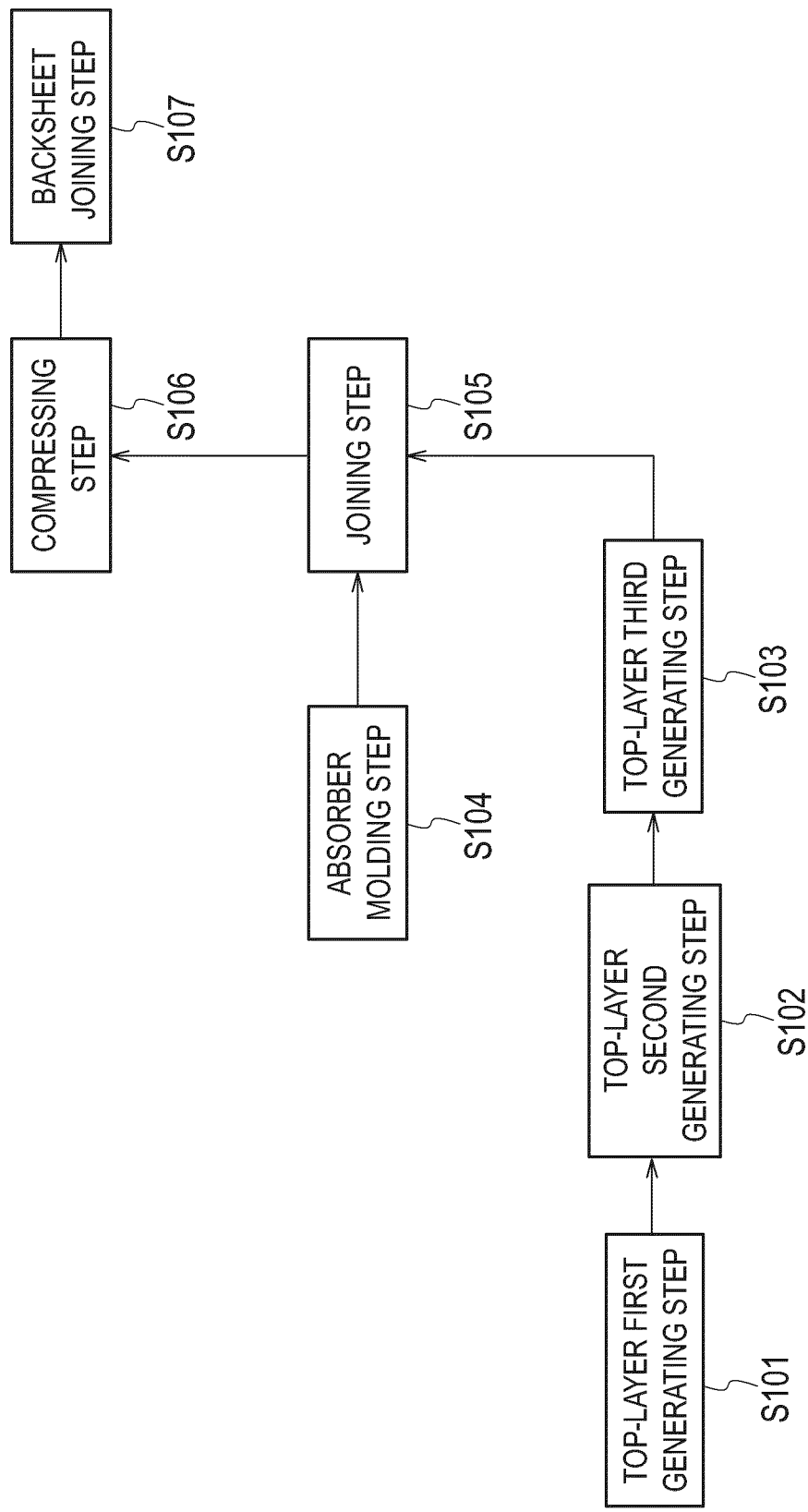

ABSORBENT ARTICLE WITH TOPSHEET, TOP-LAYER SHEET AND COMPRESSING PORTIONS

RELATED APPLICATION

This application is a 35 U.S.C. §371 national phase filing of International Patent Application No. PCT/JP2012/062344, filed May 15, 2012, through which and to which priority is claimed under 35 U.S.C. §119 to Japanese Patent Application No. 2011-113832, filed May 20, 2011.

TECHNICAL FIELD

The present invention relates to an absorbent article, and particularly relates to an absorbent article by which it is possible to improve the retention of bodily fluid discharged from an excretion portion.

BACKGROUND ART

Patent Document 1 describes a sanitary napkin having a second sheet between a topsheet and an absorber, in a sanitary napkin used as an absorbent article having a liquid-permeable topsheet, a liquid-impermeable backsheet, and an absorber arranged between the topsheet and the backsheet. The second sheet of the Patent Document 1 includes a porous nonwoven fabric or a mesh film, and is used to quickly transfer the bodily fluid that has passed through the topsheet to the absorber.

PRIOR ART DOCUMENT

Patent Document

[Patent Document 1] Japanese Unexamined Patent Application Publication No. 2006-14880 (Page 4, FIG. 2, etc.)

SUMMARY OF INVENTION

However, the applicants faced the following problem as regard the above absorbent article.

The menstrual blood absorbed into the sanitary napkin has a higher viscosity as compared to bodily fluid such as sweat. Such bodily fluid having a relatively high viscosity is retained easily in void zones such as the gaps between fibers rather than the portions with high density in which fibers are close together. However, because the second sheet of the Patent Document 1 is sandwiched by the topsheet and the absorber, the void zones of the second sheet reduce. Therefore, the amount of bodily fluid retained temporarily reduces, and the bodily fluid may leak if a large amount of bodily fluid is discharged at once.

The present invention has been achieved in view of the above-described problem and an object thereof is to provide an absorbent article by which it is possible to improve the retention of bodily fluid such as menstrual blood with a high viscosity, and prevent the leakage of the bodily fluid.

In order to resolve the above-described problems, there is provided an absorbent article (1), including: a liquid-permeable topsheet (10), a liquid-impermeable backsheet (20), and an absorber (30) arranged between the topsheet and the backsheet, wherein a liquid-permeable top-layer sheet (70) is provided at the skin contact surface side of the topsheet, and the top-layer sheet is arranged along a lengthwise direction (L) of the absorbent article at a widthwise (W) central portion of the absorbent article, and has a central region (A3) including an excretion-portion contact region arranged facing an excretion portion of a wearer, and a top-layer compressing portion (71) in which the topsheet and the top-layer sheet are compressed thickness-wise direction, and an absorber compressing portion in which at least the topsheet and the absorber are compressed thickness-wise direction are formed in the absorbent article, and the absorber compressing portion has a lengthwise compressing portion (81) along the lengthwise direction of the absorbent article at outboard of the top-layer sheet in the widthwise direction.

BRIEF DESCRIPTION OF DRAWINGS

FIG. 7 is a diagram for explaining a method of manufacturing the absorbent article according to the embodiment of the present invention.

DESCRIPTION OF EMBODIMENTS

First Embodiment

Figure 1:
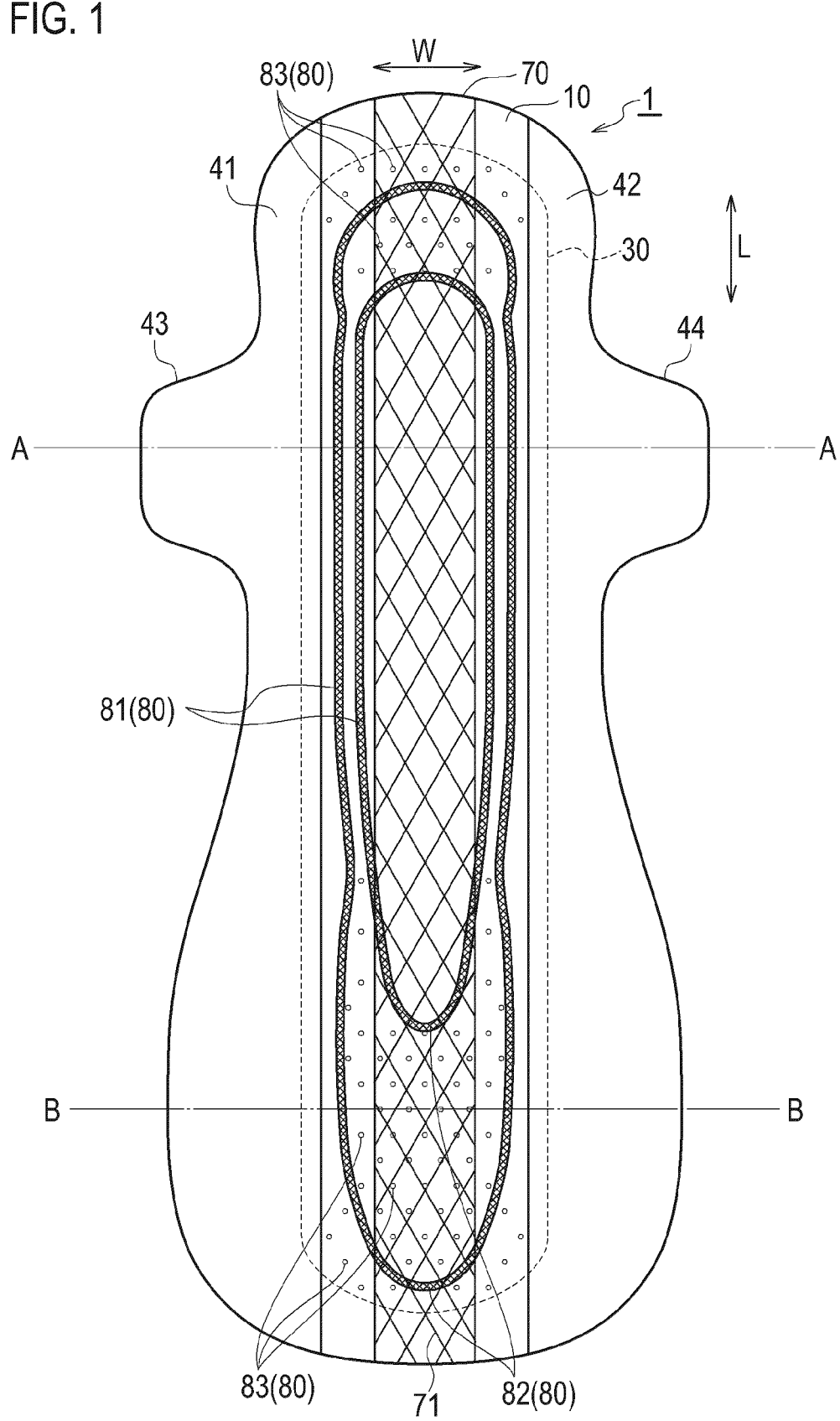
FIG. 1 is a plan view in which an absorbent article according to a first embodiment of the present invention is seen from a skin contact surface side.
Figure 2:
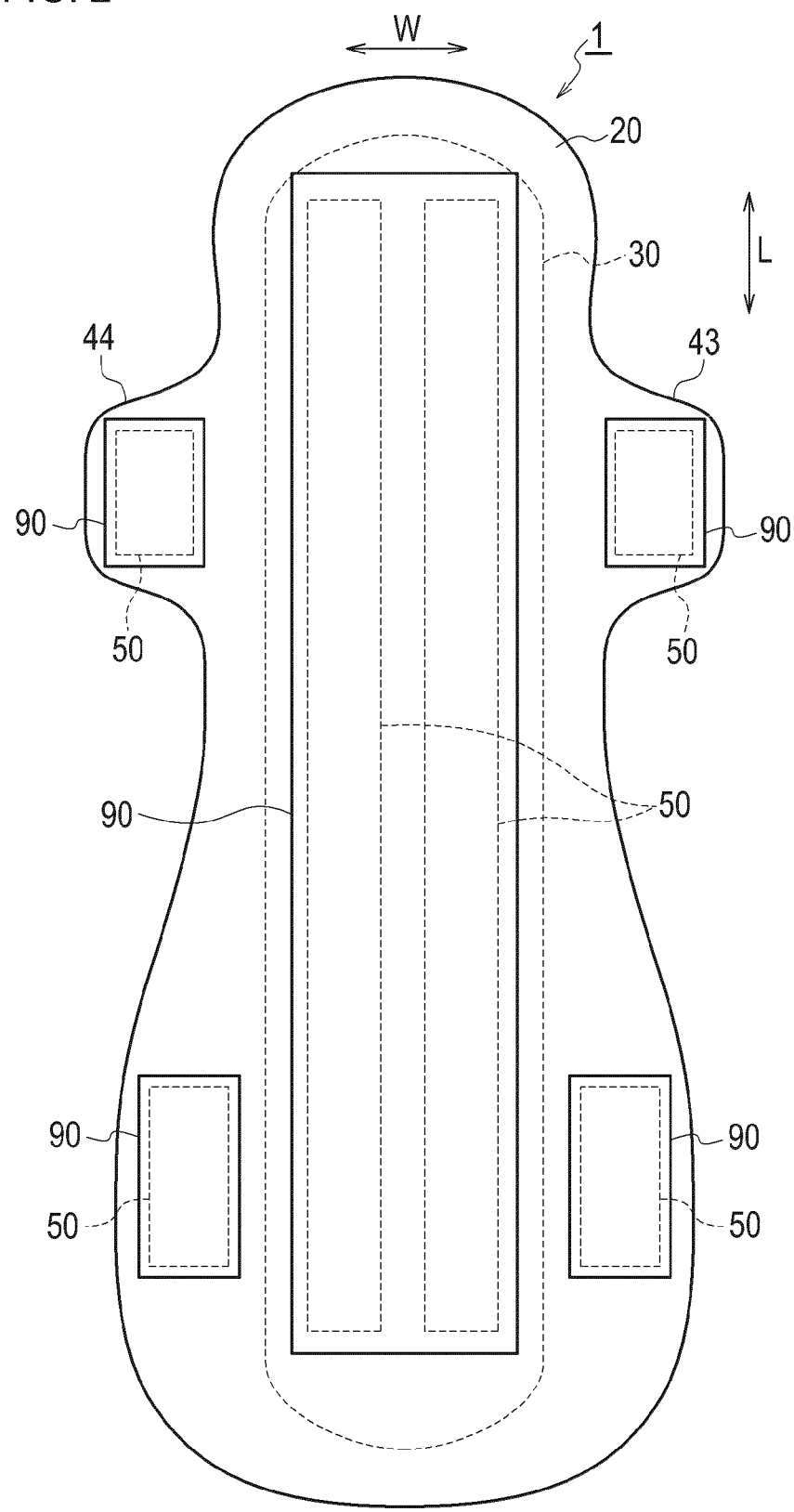
FIG. 2 is a back view of the absorbent article shown in FIG. 1.
Figure 3:
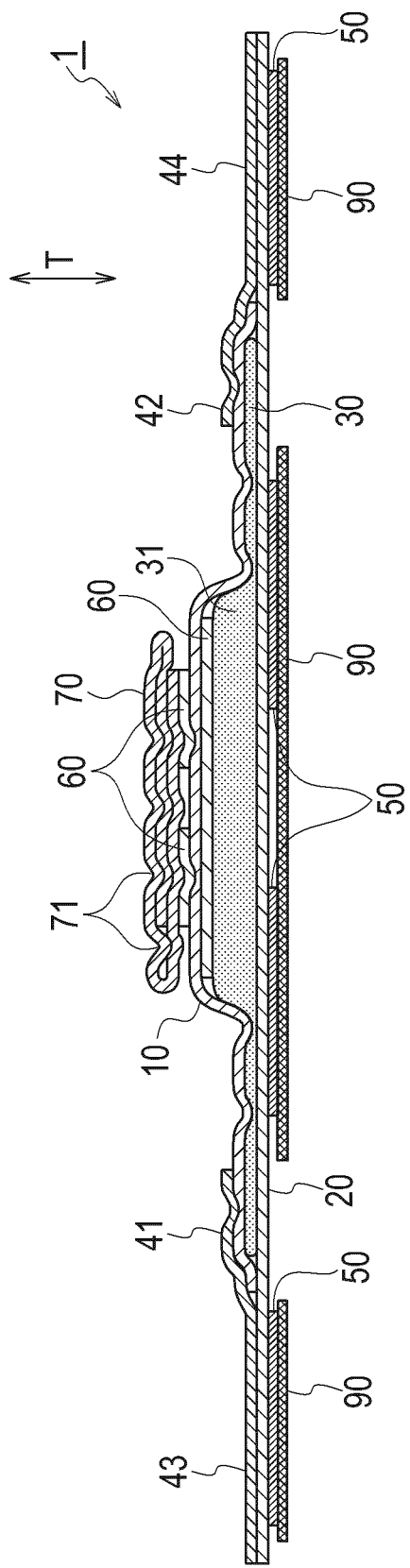
FIG. 3 is a schematic cross-sectional view of an A-A cross-section shown in FIG. 1.
Figure 4:
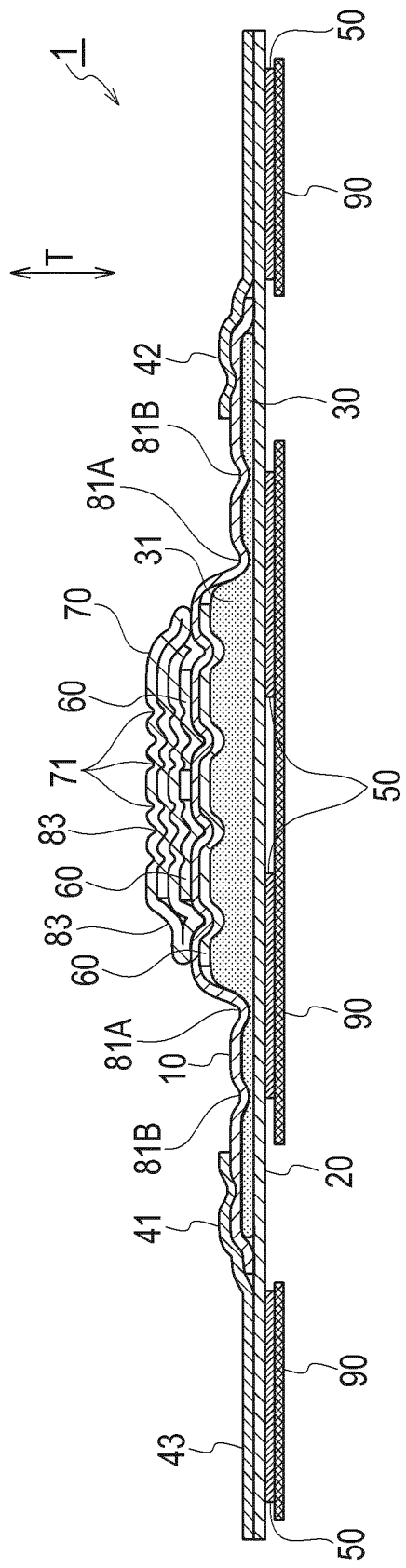
FIG. 4 is a schematic cross-sectional view of a B-B cross-section shown in FIG. 1.

An absorbent article 1 according to a first embodiment of the present invention is described with reference to FIG. 1 and FIG. 2. FIG. 1 is a plan view of the absorbent article, and FIG. 2 is a back view of the absorbent article. FIG. 3 is an A-A cross-sectional view shown in FIG. 1, and FIG. 4 is a B-B cross-sectional view shown in FIG. 1. The absorbent article 1 according to this embodiment is a sanitary napkin, for example.

The absorbent article according to the embodiment is a sanitary napkin for nighttime use. Therefore, in the absorbent article according to this embodiment, a length of the back region positioned in back of the wearer is longer than a length of the front region positioned in front of the wearer. Note that the region between a pair of wing portions described later is a region including an excretion-portion contact region with which the excretion portion of the wearer is in contact, and the front of the region forms the front region while the back of the region forms the back region. Note that in the present embodiment, a sanitary napkin for nighttime use has been explained as an example; however, the absorbent article according to the present invention can also be applied to a sanitary napkin for daytime use. As compared to the sanitary napkin according to the present embodiment, a sanitary napkin for daytime use has a short lengthwise length of the back region. For example, the length of the back region of the sanitary napkin for daytime use is substantially the same as the length of the front region.

The absorbent article 1 has a topsheet 10 that is in contact with the skin of the wearer, a liquid-impermeable backsheet 20 that does not allow liquid to pass through, and an absorber 30. The absorber 30 is arranged between the topsheet 10 and the backsheet 20. Therefore, the absorber 30 is shown with dashed lines in FIG. 1 and FIG. 2. The absorber 30 is arranged in the central portion of the lengthwise direction L and the widthwise direction W of the absorbent article 1. A liquid-permeable top-layer sheet is joined with the skin contact surface side of the topsheet 10.

In the plan view of FIG. 1, the absorbent article 1 includes wing portions 43 and 44 provided on the outer side of the absorber 30 in the widthwise direction W that is perpendicular to the lengthwise direction L. Additionally, the absorbent article 1 includes sidesheets 41 and 42 provided on the outer side of the absorber 30 in the widthwise direction W.

The topsheet 10 is a liquid-permeable sheet that allows liquids such as bodily fluid to pass through. The topsheet 10 covers at least the surface of the absorber 30. A material of the topsheet 10 is not particularly limited as long as the it is a sheet with a liquid-permable structure, such as a nonwoven fabric, a woven fabric, a porous plastic sheet, and a mesh sheet, or the like. Any natural fiber and chemical fiber may be used as a material of the woven fabric and the nonwoven fabric.

The backsheet 20 has substantially the same length as the length of the topsheet 10. As for the backsheet 20, a polyethylene sheet, a laminated nonwoven fabric with polypropylene as the main constituent, an air-permeable resin film, or a sheet in which an air-permeable resin film is joined with a nonwoven fabric such as spun bond or spun lace can be used. A material of the backsheet 20 is desired to be a material having flexibility to an extent such that a discomfort is not created at the time of wearing. The backsheet 20 is desired to have liquid impermeability and moisture permeability, and for example, can be configured from a microporous sheet obtained by melt-mixing an inorganic filler in an olefin resin such as polyethylene and polypropylene, and then performing stretch processing.

The absorber 30 includes hydrophilic fibers and pulp. The absorber 30 is formed of a material that can absorb bodily fluid such as menstrual blood. The absorber 30 may be formed by layering a hydrophilic fiber or a powder with an air-laid method, or the absorber may be an air-laid sheet in which a hydrophilic fiber or a powder is shaped into a sheet with an air-laid method, or the absorber may be formed by arranging a ground pulp mixed with a high absorbent polymer on a tissue (for example, 15 g/m$^2$ basis weight), and then wrapping it up with the tissue.

The absorber 30 according to the present embodiment is configured by wrapping pulp 8, which is formed by layering cotton-like pulp and synthetic pulp at a basis weight of approximately 100 to 300 g/m$^2$, with a protective sheet (not shown in the figure). The thickness of a core unit 31 (for example, see FIG. 3) positioned in the widthwise center of the absorber 30 is more than the thickness of widthwise both sides. Note that the absorber 30 may have a substantially uniform thickness on the entire surface, or may have a non-uniform thickness. The protective sheet is used to retain the shape of the pulp, and for example, a crepe paper and tissue paper, or the like can be used.

The absorber 30 has a shape extending front-back wise and is smaller by substantially one size than the backsheet 20. The length of the absorber 30 in the widthwise direction W corresponds to the length of crotch in the widthwise direction of an adult female, and is generally between 50 and 80 mm. The absorber 30 is bonded to the backsheet 20 by an adhesive such as a hot-melt adhesive. Furthermore, in the present embodiment, the absorber 30 and the topsheet 10 are bonded by a hot-melt adhesive 60 (see FIG. 3).

The core unit 31 is provided to include the center of the excretion-portion contact region with which at least the excretion portion of the wearer is in contact. The center of the excretion-portion contact region is the lengthwise and widthwise center of the region with which the excretion portion of the wearer is in contact. For example, in an absorbent article having wing portions, the lengthwise center of the wing portions is the lengthwise center of the excretion-portion contact region. Furthermore, in an absorbent article that does not have wing portions, the position where the widthwise length dimension of the absorber is the shortest is the lengthwise center of the excretion-portion contact region. The excretion-portion contact region is included in the region that is in contact with the crotch portion of the wearer, and is positioned between both legs of the wearer.

The sidesheets 41 and 42 are arranged on both sides of the topsheet 10. The sidesheets 41 and 42 can be formed by the same material as the topsheet 10. However, in order to prevent the flow of menstrual blood outside the absorbent article 1 by crossing over the sidesheets 41 and 42, the sidesheets are desired to have a hydrophobic property or water repellency. The sidesheets 41 and 42 cover a part of the side edges of the absorber 30, and the wing portions 43 and 44.

In the absorbent article 1, the peripheries of the topsheet 10, the sidesheets 41 and 42, and the backsheet 20 are joined, and the absorber 30 is included within. As for the method of joining the topsheet 10 and the backsheet 20, any one of heat embossing, supersonic waves, or a hot-melt adhesive, or a combination of a plurality of methods can be used.

In the backsheet 20, an adhesive member 50 is applied in a plurality of regions on the surface that is in contact with the underwear (see FIG. 2). The adhesive member 50 is provided intermittently along the lengthwise direction L in the back side of the absorber. The adhesive member 50 is also provided on the surface that is in contact with the underwear in the wing portion 43 and the wing portion 44. In the state prior to use, the adhesive member 50 is in contact with a release sheet 90. The release sheet 90 prevents the degradation of the adhesive member 50 before use. Also, at the time of use, the release sheet 90 is peeled by the wearer.

Note that in an absorbent article that does not have the release sheet 90; the configuration may be such that the degradation of the adhesive member before use may be prevented by a packaging sheet used to individually package the absorbent article. When the adhesive member and the packaging sheet are in contact, it is desired to perform a process on the surface of the packaging sheet to enable peeling of the adhesive member without causing a decline in the adhesive power of the adhesive member.

The top-layer sheet 70 is a liquid-permeable sheet that allows liquids such as bodily fluid to pass through. The top-layer sheet 70 is not particularly limited as long as the top-layer sheet 70 is a sheet-like material having a structure that allows the liquids to pass through, such as a nonwoven fabric, a woven fabric, a perforated plastic sheet, and a mesh sheet. Natural fibers or chemical fibers can be used as a woven and nonwoven fabric. The top-layer sheet 70 is folded with a fold extending in the lengthwise direction L as a base point, and is layered into two or three layers in the thickness direction T of the absorbent article.

By thus folding and layering the top-layer sheet 70, the bulk of the top-layer sheet 70 is maintained, and gaps within the top-layer sheet 70 can be secured. The layers of the folded top-layer sheet are joined to each other by a hot-melt adhesive.

The hot-melt adhesive between the layers of the top-layer sheet 70 is desired to be provided lengthwise. In cases where the adhesive is hydrophobic in nature, when the bodily fluid discharged from the excretion portion is retained by the top-layer sheet, the bodily fluid can be diffused lengthwise by avoiding the hydrophobic bonded region (along the bonded region).

Note that in the present embodiment, the top-layer sheet 70 is configured by being layered, however, for example, in cases where a relatively bulky sheet material is used, the top-layer sheet need not necessarily be layered as long as the configuration is such that gaps can be secured. The top-layer sheet 70 according to the present embodiment is an air-through nonwoven fabric having a basis weight of 20 g/m$^2$, and is formed from composite fibers having a core-clad structure with a core of 2.2-dtex PET (polyethylene terephthalate) and a clad of PE (polyethylene). A bulk recovery process (leaving to stand for 10 minutes at a temperature of) 90° is performed for the nonwoven fabric, and adjustments are made such that the density becomes 0.025 g/cm$^3$. By thus performing the bulk recovery process in the top-layer sheet, the gaps within the top-layer sheet are increased and the retention of the bodily fluid can be improved. Furthermore, the air-through nonwoven fabric is a nonwoven fabric with a relatively large number of gaps, which can enable relatively improved retention of the bodily fluid.

Furthermore, the topsheet 10 according to the present embodiment is an air-through nonwoven fabric having a basis weight of 25 g/m$^2$, and is formed from composite fibers having a core-clad structure with a core of 2.2-dtex PET and a clad of PE. Note that the bulk recovery process is not performed for the topsheet, and the density of the topsheet is 0.055 g/cm$^3$.

By thus configuring the fiber density of the topsheet 10 higher than the fiber density of the top-layer sheet, the bodily fluid can be transferred smoothly from the top-layer sheet 70 to the topsheet 10 as a result of a density gradient. Furthermore, due to a decline in the density of the top-layer sheet as a result of the bulk recovery process, a density difference is provided with respect to the topsheet, and the bodily fluid can be transferred smoothly from the top-layer sheet to the topsheet because of the density gradient. Specifically, the bodily fluid retained by the top-layer sheet having a low density can be transferred to the topsheet having a high density.

The top-layer sheet 70 is joined with the skin contact surface side of the topsheet 10, and is arranged along the lengthwise direction L of the absorbent article 1 in the widthwise central portion of the absorbent article 1. The length of the top-layer sheet 70 in the lengthwise direction L is substantially same as the length of the absorbent article 1 in the lengthwise direction L, and the length of the top-layer sheet 70 in the widthwise direction W is shorter than the length of the absorbent article 1 in the widthwise direction W, and shorter than the length of the absorber 30 in the widthwise direction W.

Figure 5:
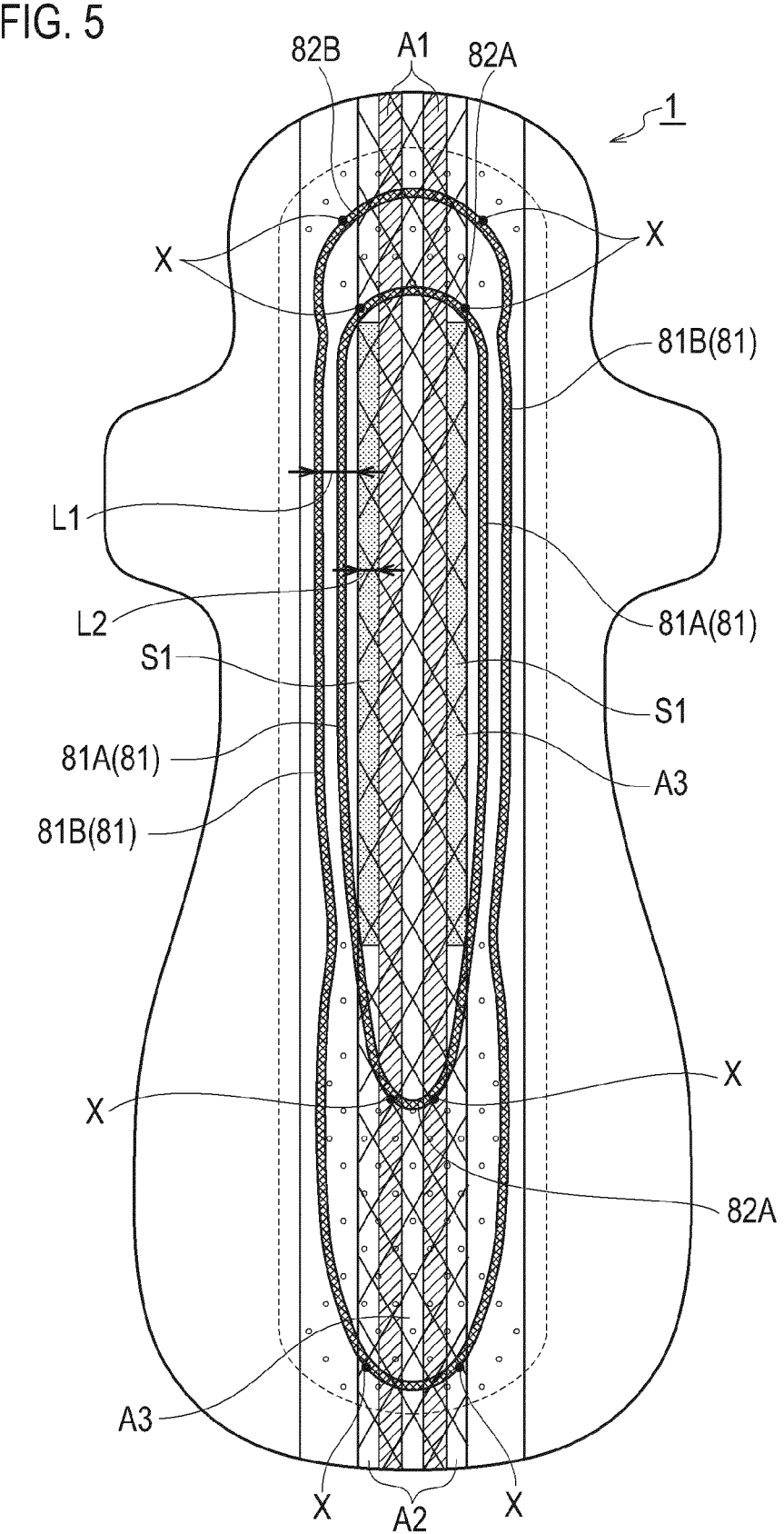
FIG. 5 is a plan view as seen from a skin contact surface side of the absorbent article according to the first embodiment.

The top-layer sheet 70 includes a bonded region A1 that is bonded to the topsheet 10 via an adhesive, and a non-bonded region A2 that is not bonded to the topsheet 10 via an adhesive. FIG. 5 is a plan view of the absorbent article shown in FIG. 1, and illustrates the bonded region A1 and the non-bonded region A2. In FIG. 5, the bonded region A1 is the hatched region. The bonded region A1 is arranged in two columns along the lengthwise direction L in the central portion W of the width direction W of the top-layer sheet 70.

The top-layer sheet 70 has a central region that includes the excretion-portion contact region arranged opposite the excretion portion of the wearer. The excretion-portion contact region is the region that is in contact with the excretion portion of the wearer. As long as a central region A3 includes at least the center of the excretion-portion contact region, the center of the central region A may coincide with the center of the excretion-portion contact region, or the center of the central region A3 may deviate from the center of the excretion-portion contact region. In the present embodiment, the region positioned on the inner side of a first lengthwise compressing portion 81A and a first widthwise compressing portion 82A, which are described later, forms the central region A3.

When the bonded regions A1 are provided in two columns widthwise, the non-bonded region A2 can be provided at both widthwise ends of the top-layer sheet and between the two columns of the bonded region A1. For example, in the bonded region A1, the sheets are bonded with each other, and gaps within the sheets may be reduced. Therefore, as compared to the non-bonded region A2, the retention of the bodily fluid may decline in the bonded region A1. However, by arranging the non-bonded region in the widthwise central portion of the absorber, the retention of the bodily fluid in the widthwise central portion of the absorber can be maintained.

Furthermore, in cases where the adhesive is hydrophobic in nature, by providing the non-bonded region extending lengthwise between the bonded regions, after the bodily fluid discharged from the excretion portion is pulled in by the top-layer sheet, the bodily fluid can be diffused lengthwise by avoiding the hydrophobic bonded region (along the bonded region). Note that in the present embodiment, the bonded region is provided in two columns and the non-bonded region is provided between the bonded regions, however, the bonded region may be provided in one column, or the bonded region may be provided in three or more columns.

In the absorbent article 1, a compressing portion 80 in which at least the topsheet 10 and the absorber 30 are compressed thickness-wise is formed. The compressing portion 80 includes a lengthwise compressing portion 81 extending along the lengthwise direction L, a widthwise compressing portion 82 extending widthwise, and a plurality of punctate compressing portions 83 formed intermittently.

The lengthwise compressing portion 81 is arranged adjacent to the top-layer sheet 70 at the widthwise outer side from the top-layer sheet 70. In the lengthwise compressing portion 81, the topsheet 10 and the absorber 30 are compressed thickness-wise. The lengthwise compressing portion 81 is formed in two columns along the lengthwise direction L, and includes a first lengthwise compressing portion 81A positioned on the widthwise inner side, and a second lengthwise compressing portion 81B arranged on the widthwise outer side from the first lengthwise compressing portion 81A.

The lengthwise compressing portion 81 is arranged adjacent to the top-layer sheet 70. In the lengthwise compressing portion 81, the absorber 30 is compressed thickness-wise, which makes it easy to pull in the bodily fluid, for example. Therefore, the bodily fluid that is retained temporarily by the top-layer sheet 70 can be pulled in near the top-layer sheet 70, and the bodily fluid retained by the top-layer sheet can be absorbed rapidly. Furthermore, the diffusion of the bodily fluid towards the widthwise outer side from the lengthwise compressing portion 81 is inhibited, and side leakage can be prevented.

The widthwise compressing portion 82 is formed along the widthwise direction W. The widthwise compressing portion 82 that is formed in the region in which the top-layer sheet 70 is arranged is formed by compressing thickness-wise the top-layer sheet 70, the topsheet 10, and the absorber 30. The widthwise compressing portion 82 that is formed in the region in which the top-layer sheet 70 is not arranged is formed by compressing the topsheet 10 and the absorber 30 thickness-wise. The widthwise compressing portion 82 is formed in two columns along the widthwise direction W, and includes a first widthwise compressing portion 82A positioned on the lengthwise inner side, and a second widthwise compressing portion 82B arranged at the lengthwise outer side from the first widthwise compressing portion.

The lengthwise compressing portion 81 may be formed at an inclination with respect to a straight line along the lengthwise direction L, and the angle (acute-angle side) formed by the straight line along the lengthwise direction L and the lengthwise compressing portion 81 is 45 degrees or less. On the other hand, the widthwise compressing portion 82 may be formed at an inclination with respect to a straight line along the widthwise direction W, and the angle (acute-angle side) formed by the straight line along the widthwise direction W and the widthwise compressing portion 82 is less than 45 degrees.

In this case, as shown in FIG. 1, the lengthwise compressing portion 81 and the widthwise compressing portion 82 may be connected to form a circular compressing portion, or may not be connected. In the present embodiment, the first lengthwise compressing portion 81A and the first widthwise compressing portion 82A are formed in continuation, and the second lengthwise compressing portion 81B and the second widthwise compressing portion 82B are formed in continuation. Furthermore, the lengthwise compressing portion and the widthwise compressing portion may be connected to form a substantially U-shaped compressing portion, or may not be connected. In FIG. 5, a boundary X between the lengthwise compressing portion and the widthwise compressing portion is illustrated.

The punctate compressing portions 83 are circular and are formed intermittently in plurality. The punctate compressing portions 83 constitute the outer circumference of the orbit-shaped compressing portion formed by the first lengthwise compressing portion 81A and the first widthwise compressing portion 82A, and are formed in the front end of the absorber 30 and the back end of the absorber 30. Note that as long as the punctate compressing portions are provided intermittently in plurality, the shape of the punctate compressing portions is not limited to circular, but can also be elliptical, start-shaped, heart-shaped, and rhomboidal-shaped.

Because the top-layer sheet, the topsheet, and the absorber are joined as one part by the punctate compressing portions in the front end of the absorber 30 and the back end of the absorber 30, the distance of the absorbing layer from the surface is reduced. The bodily fluid that is discharged from the wearer and flows towards the back is retained in the gap within the top-layer sheet, and can be pulled in by the punctate compressing portions 83. Because the punctate compressing portions 83 are interspersed, the punctate compressing portions easily come in contact with the bodily fluid flowing in any direction, and easily pull in the bodily fluid.

Because the punctate compressing portions are arranged intermittently, it is difficult for the punctate compressing portions to become harder than the widthwise compressing portion extending widthwise and the lengthwise compressing portion extending lengthwise. However, the punctate compressing portions can prevent the hardening as a result of some regions from becoming deviated in rigidity, and can control the deterioration in the comfort when wearing the absorbent article.

Furthermore, for example, when the compressing portions extend widthwise and also extend lengthwise, the bodily fluid retained by the compressing portions may get diffused front-back-wise and widthwise. Particularly, the punctate compressing portions 83 are arranged in the front end of the absorber 30 and the back end of the absorber 30, and when the bodily fluid is over-diffused, front leakage, for example, may occur. However, because the punctate compressing portions are circular, the diffusion of the retained bodily fluid is controlled, and leakage can be prevented.

Note that in a region where the top-layer sheet 70 is arranged, the compressing portion 80 is formed by compressing the top-layer sheet 70, the topsheet 10, and the absorber 30 thickness-wise, and in a region where the top-layer sheet 70 is not arranged, the compressing portion 80 is formed by compressing the topsheet 10 and the absorber 30 thickness-wise.

The portion of the top-layer sheet 70 where the compressing portion 80 is formed is joined with the topsheet 10 by a compression process. Therefore, a non-joined region S1 in which the top-layer sheet 70 and the topsheet 10 are not joined is the non-bonded region A2 in which the topsheet 10 and the top-layer sheet 70 are not joined by an adhesive, and is the region where the compressing portion 80 is not formed. The non-joined region S1 is the dotted region of FIG. 5. Note that the so-called region in which the compressing portion is not formed is the region between compressing portions that is formed lengthwise in the top-layer sheet. The non-joined region S1 is the region in which the topsheet and the top-layer sheet are not joined by an adhesive, and where the compressing portion 80 is not formed, and also includes the portion joined by the top-layer compressing portion 71 in cases where the top-layer sheet and the topsheet are joined partially by the top-layer compressing portion 71.

The compressing portion 80 is a portion with a relatively high density in which at least the topsheet 10 and the absorber 30 are compressed and formed thickness-wise. By forming the compressing portion 80 in the periphery of the non-joined region S1 of the top-layer sheet 70, the bodily fluid retained temporarily by the top-layer sheet 70 can be pulled in by a compressing portion having a relatively high density. For example, because the lengthwise compressing portion 81 is formed at the widthwise outer side of the non-joined region S1, side leakage can be prevented, and because the widthwise compressing portion 82 is formed on the outer side of the lengthwise of the non-joined region S1, front leakage and leakage from the hip portion can be prevented.

Furthermore, the compressing portion 80 is a relatively hard portion in which at least the topsheet 10 and the absorber 30 are compressed and formed thickness-wise. Because the lengthwise compressing portion 81 is formed at the widthwise outer side of the top-layer sheet 70, when pressure is applied from the widthwise outer side towards the inner side, deformation occurs towards the inner side with the lengthwise compressing portion 81 as the base point, and the external force can be absorbed. Furthermore, because the widthwise compressing portion extending widthwise is formed, the resistance to the force from the widthwise outer side increases. Therefore, when force is applied from both widthwise outer sides towards the inner side of the absorbent article 1, such as when the wearer wearing the absorbent article 1 closes both the legs, the deformation of the absorber can be controlled.

In the top-layer sheet 70, a top-layer compressing portion 71 in which the topsheet 10 and the top-layer sheet 70 are compressed thickness-wise is formed. The top-layer compressing portion 71 is arranged in the shape of a lattice. In the portion in which the top-layer compressing portion 71 is formed, the topsheet 10 and the top-layer sheet 70 are compressed and brought close. Therefore, by forming the top-layer compressing portion 71, the transfer of the bodily fluid from the top-layer sheet 70 to the topsheet 10 can be improved. On the other hand, because gaps can be retained in the portion other than the top-layer compressing portion 71 of the top-layer sheet 70, the temporary retention of the bodily fluid can be maintained.

The top-layer compressing portion 71 is arranged at an inclination with respect to the lengthwise direction L. Therefore, when the absorbent article 1 is pressed from the widthwise outer side towards the inner side, the absorbent article twists easily along the inclined top-layer compressing portion 71, and the lengthwise twisting of the absorbent article can be prevented. Furthermore, because the lattice of the top-layer compressing portion is rhomboidal in shape with the lengthwise direction being longer than the widthwise direction, it becomes difficult for the bodily fluid to diffuse widthwise.

Figure 6A:
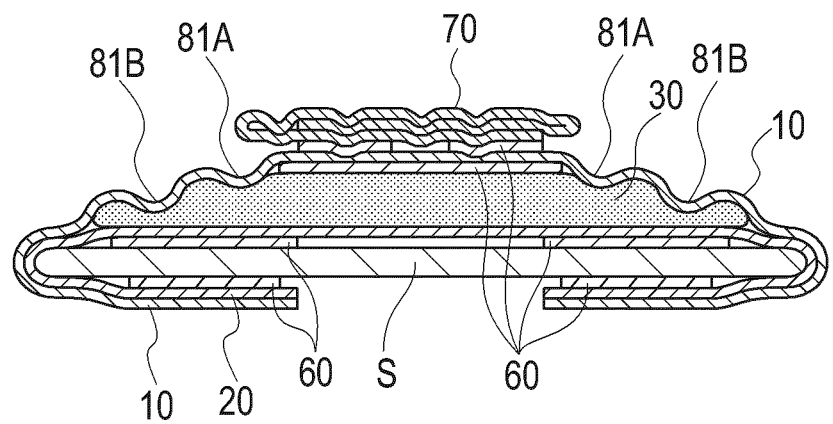
FIG. 6A is a cross-sectional view schematically showing a state when the absorbent article shown in FIG. 1 is worn.
Figure 6B:
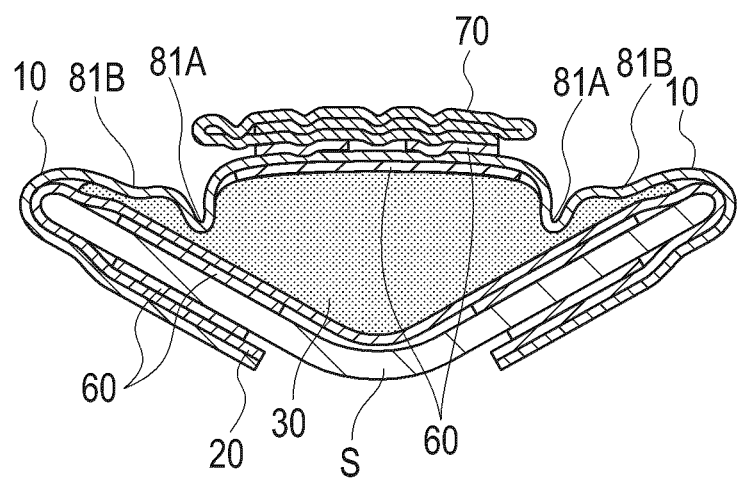
FIG. 6B is a cross-sectional view schematically showing a state when the absorbent article shown in FIG. 1 is worn.

FIG. 6A and FIG. 6B are a view of the A-A cross section of FIG. 1 that schematically illustrates the state when the absorbent article is worn. FIG. 6A illustrates the state when the absorbent article 1 is worn in underwear S. The wing portions 43 and 44 arranged on the widthwise outer side of the absorbent article 1 are folded back towards the back side of the underwear. FIG. 6B illustrates the state when the absorbent article 1 is pressed from the widthwise outer side towards the inner side.

When the absorbent article 1 is pressed from the widthwise outer side towards the inner side, the absorbent article 1 gets deformed towards the inner side with the base points as the first lengthwise compressing portion 81A and the second lengthwise compressing portion 81B.

The top-layer sheet 70 is joined with the topsheet 10 at only the widthwise central portion of the absorber 30, and the non-bonded region A2 is arranged on both the sides. Therefore, the top-layer sheet 70 of the bonded region A1 is pushed up together with the topsheet 10, and the top-layer sheet 70 of the non-bonded region A2 is separated from the topsheet 10 and pushed up in a level state. As a result of being deformed in such a way, the top-layer sheet 70 is maintained in a state facing the body of the wearer, such as the excretion portion. Furthermore, because the top-layer sheet 70 is pushed up towards the wearer (upper side), the top-layer sheet 70 can be brought close to the excretion portion, and the bodily fluid excreted from the excretion portion can be pulled in quickly into the top-layer sheet.

Furthermore, the absorbent article 1 is configured such that the absorbent article 1 is deformed towards the widthwise inner side with the base point as the first lengthwise compressing portion 81A that is adjacent to the top-layer sheet 70 at the widthwise outer side from the top-layer sheet 70, and the absorber 30 absorbs the external force exerted from the widthwise outer side towards the inner side. Therefore, when force is applied from both widthwise outer sides towards the inner side of the absorbent article 1, such as when the wearer wearing the absorbent article 1 closes both the legs, the deformation of the top-layer sheet 70 can be controlled. Furthermore, because the lengthwise compressing portion 81 is formed by extending lengthwise spanning at least the excretion-portion contact region, the top-layer sheet can be arranged facing at least the excretion portion of the wearer.

Because the non-joined region S1 of the top-layer sheet is not joined with the topsheet 10, the deformation of the top-layer sheet that is based on the deformation of the topsheet, for example, can be reduced when the absorbent article is pressed from the widthwise outer side towards the inner side. Therefore, it becomes easy to maintain the top-layer sheet in a state facing the body of the wearer, such as the excretion portion.

A length L1 between the end at the lengthwise compressing portion side of the top-layer sheet 70 and the end at the widthwise outer side of the lengthwise compressing portion is longer than a widthwise length L2 of the non-joined region. Because the length L1 is longer than the length L2, even when the absorbent article 1 is pressed from the widthwise outer side towards the inner side, and the absorbent article is deformed such that the compressing portion on the lengthwise outer side moves towards the widthwise inner side, the lengthwise compressing portion 81 is arranged on the widthwise outer side from the top-layer sheet 70. Therefore, the bodily fluid that is retained temporarily by the top-layer sheet 70 is pulled in by the lengthwise compressing portion 81, and side leakage can be prevented. Note that when two ends are formed at the widthwise outer side of the lengthwise compressing portion 81, the end that is positioned at the outermost side is taken into consideration.

On the other hand, the punctate compressing portions 83 are formed in the front end and back end of the absorber, and the front end and back end of the absorber do not twist easily widthwise and do not twist easily lengthwise. Therefore, the absorber 30 curves easily front-back-wise along the outer shape of the body of the wearer, and the fitting of the absorbent article can be improved.

Note that as long as the compressing portions are formed by compressing at least the topsheet 10 and the absorber 30 in the thickness direction T, various configurations can be adopted. For example, the compressing portions may be formed by pressing and embossing, and the shape may be a lattice network and a honeycomb shape.

Note that the hardness of the absorbent article can be measured by using the Gurley method stipulated in JIS-1096, for example. Furthermore, the basis weight and density of the absorber can be measured by the following measurement method, for example. In an absorbent article packaged by a package, the package is opened and the folded absorbent article is expanded, and then the thickness and the area of the portion whose basis weight and density are to be measured are measured. Next, the portion whose basis weight and density are to be measured is cut out from the absorbent article, and then the weight of the cut-out portion is measured. Next, the portions other than the absorber, such as the topsheet and the backsheet, are removed from the cut-out portion, and then the weight of the absorber is measured. The basis weight is calculated based on the weight of the absorber and the area of the portion whose basis weight and density are to be measured. The density is calculated based on the basis weight and thickness.

Note that the thickness can be measured by the following measurement method. Specifically, after the sample absorbent article is frozen by immersing it in liquid nitrogen, the sample is cut with a blade, the sample is returned to the normal temperature, and then the resultant sample is measured at 50 times magnification by using a microscope (such as Keyence-make VE7800). Here, the reason for freezing the sample absorbent article is to prevent variation in the thickness due to compression during cutting.

Next, a part of the method of manufacturing the absorbent article 1 according to the present embodiment is described with reference to FIG. 7. Note that as far as the method that is not described in FIG. 7 is concerned, the existing method can be used. As shown in FIG. 7, in the method of manufacturing the absorbent article, a top-layer first generating step is performed in step 101. Specifically, in the top-layer first generating step, after performing the bulk recovery process in the top-layer sheet 70, the top-layer sheet is folded at three folds. Also, the top-layer sheet 70 is bonded on top of the topsheet 10 via the hot-melt adhesive 60. The bulk recovery process is performed by passing the top-layer sheet through a container in which hot air is being supplied, for example.

Next, in step 102, a top-layer second generating step is performed. Specifically, the topsheet 10 and the top-layer sheet 70 are compressed in the thickness-wise direction T, and the top-layer compressing portion 71 is formed. In this compression process, for example, the top-layer sheet 70 and the topsheet 10 are passed through an embossing roller that performs heating and pressing (the top-layer sheet side has a convex pattern, and the topsheet side has a flat pattern), and lattice embossing is formed.

In step 103, a top-layer third generating step is performed. Specifically, the topsheet and the sidesheets 41 and 42 are bonded by heat sealing, for example.

Next, in step 104, an absorber molding step is performed. Specifically, the absorber 30 is molded by a molding drum, by molding the pulp that is the raw material of the absorber. Note that the order of the top-layer generating steps performed in steps 101 through 103 and the absorber molding step performed in step 104 may be in a reverse order.

In step 105, a joining step is performed. Specifically, the joining step of joining the top layer generated in step 103 and the absorber 30 molded in step 104 is performed.

In step 106, a compressing step is performed. Specifically, the absorber 30 and the topsheet 10 are compressed thickness-wise, and the top-layer sheet, the topsheet, and the absorber 30 are compressed thickness-wise to form the compressing portion 80. In step 107, a backsheet joining step is performed. Specifically, the absorber and the topsheet in which the compressing portion is formed in step 106 are joined with the backsheet. Note that in FIG. 7, although not shown in the figure, after joining the backsheet, a step of applying an adhesive is provided. The absorbent article according to the present embodiment can thus be manufactured by the aforementioned steps.

Second Embodiment

Figure 8:
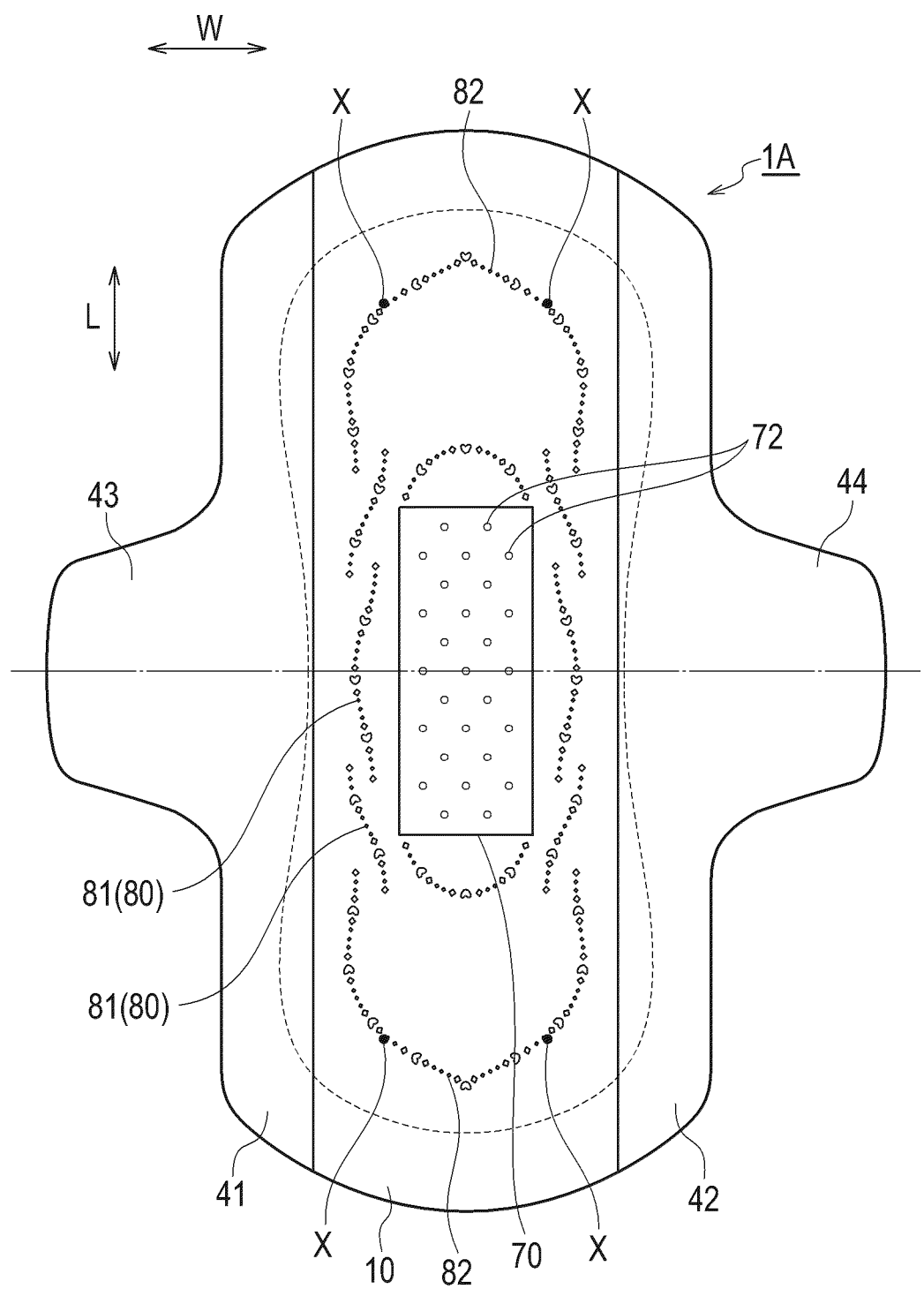
FIG. 8 is a plan view in which an absorbent article according to a second embodiment of the present invention is seen from a skin contact surface side

Next, an absorbent article 1A according to a second embodiment is explained based on FIG. 8. The absorbent article 1A according to the second embodiment is a sanitary napkin for daytime use. In the absorbent article 1A according to the second embodiment, the length of the back region of the absorbent article is substantially the same as the length of the front region. In the second embodiment, the same symbols have been used for the configuration that is the same as the first embodiment, and the explanation has been omitted.

The lengthwise length of the top-layer sheet 70 of the absorbent article according to the second embodiment is shorter than the lengthwise length of the absorbent article. The top-layer sheet 70 is in the lengthwise center of the absorber 30, and is arranged in the widthwise center thereof, and is also arranged to cover the excretion-portion contact region. In the top-layer sheet 70, along with the topsheet 10, a punctate compressing portion 72 that is compressed thickness-wise is formed. The top-layer sheet 70 and the topsheet 10 are joined by this punctate compressing portion.

As mentioned above, although the content of the present invention was disclosed through the embodiments of the present invention, the descriptions and drawings that form a part of this disclosure are not to be considered as limitation to the present invention. From this disclosure, a variety of alternate embodiments, examples, and applicable techniques will become apparent to one skilled in the art.

For example, the lengthwise compressing portions according to the present embodiment include the two compressing portions of the first lengthwise compressing portion and the second lengthwise compressing portion, however, there may be a single compressing portion. Furthermore, for example, in the absorbent article, gathers may be formed at the widthwise outer end of the absorber.

In the present embodiment, the absorber and the topsheet are bonded via an adhesive, however, the absorber and the topsheet may not be joined in at least the lower side of the non-joined region. Due to the fact that the absorber and the top-layer sheet are not joined in the lower side (a non-skin contact surface side) of the non-joined region, the deformation of the top-layer sheet that is based on the deformation of the absorber can be reduced when the absorbent article is pressed from the widthwise outer side towards the inner side.

Specifically, if the absorbent article is pressed from the widthwise outer side towards the inner side, the widthwise length of the absorber becomes short, and the thickness increases. Therefore, the topsheet and the top-layer sheet arranged on the absorber are pushed upwards. At this time, because the topsheet is arranged on top of the absorber without being joined with the absorber, the topsheet is pushed up as a result of the thickness-wise deformation of the absorber, without being receiving a widthwise influence of the absorber. Therefore, the top-layer sheet is also pushed up, and it becomes easy to maintain the top-layer sheet in a state facing the body of the wearer, such as the excretion portion.

The entire contents of Japanese Patent Application No. 2011-113832 (filed on May 20, 2011) are incorporated in the present specification by reference.

INDUSTRIAL APPLICABILITY

The present invention can temporarily retain the bodily fluid excreted from the excretion portion with the help of the top-layer sheet joined on top of the topsheet. Because the top-layer sheet is not sandwiched by the topsheet, for example, it is easy to secure gaps within the top-layer sheet. As a result of the gaps in the top-layer sheet, the temporarily-stored amount of the bodily fluid, such as menstrual blood having a relatively high viscosity, increases. Therefore, even when a large amount of bodily fluid is discharged at once, the leakage of the bodily fluid can be prevented. A lengthwise compressing portion is provided at the widthwise outer side of the top-layer sheet. The lengthwise compressing portion is a portion with a relatively high density in which at least the topsheet and the absorber are compressed thickness-wise. Because this compressing portion is arranged on the widthwise outer side of the top-layer sheet, the bodily fluid collected by the top-layer sheet can be pulled in by the lengthwise compressing portion having a relatively high density. Because the lengthwise compressing portion can pull in the bodily fluid, an absorbent article that can prevent the leakage of the bodily fluid can be provided.

REFERENCE SIGN LIST

A1 bonded region
A2 non-bonded region
L lengthwise direction
S1 non-joined region
T thickness-wise direction
W widthwise direction
X boundary
1 absorbent article
10 topsheet
20 backsheet
30 absorber
31 core unit
41, 42 sidesheets
43, 44 wing portions
50 adhesive member
60 hot-melt adhesive
70 top-layer sheet
71 top-layer compressing portion
80 compressing portion
81 lengthwise compressing portion
81A first lengthwise compressing portion
81B second lengthwise compressing portion
82 widthwise compressing portion
82A first widthwise compressing portion
82B second widthwise compressing portion
83 punctate compressing portions
90 release sheet

The invention claimed is:

1. An absorbent article, comprising: a liquid-permeable topsheet, a liquid-impermeable backsheet, and an absorber arranged between the topsheet and the backsheet, wherein
a liquid-permeable top-layer sheet is provided at the skin contact surface side of the topsheet, and
the top-layer sheet is arranged along a lengthwise direction of the absorbent article at a widthwise central portion of the absorbent article, and has a central region including an excretion-portion contact region configured to be arranged opposite an excretion portion of a wearer in use, and
a top-layer compressing portion within the central region in which only the topsheet and the top-layer sheet are compressed thickness-wise, and an absorber compressing portion outboard of the central region in which at least the topsheet and the absorber are compressed thickness-wise are formed in the absorbent article,
the absorber compressing portion has a lengthwise compressing portion along the lengthwise direction of the absorbent article outboard of the top-layer sheet in the widthwise direction,
wherein the absorber compressing portion has a plurality of punctate compressing portions in the shape of dots that are formed intermittently outboard of the central region in the lengthwise direction, and
in the punctate compressing portions, the top-layer sheet, the topsheet, and the absorber are compressed thickness-wise.

2. The absorbent article according to claim 1, wherein the absorber compressing portion has a widthwise compressing portion extending in a widthwise direction outboard of the central region in the lengthwise direction, and
in the widthwise compressing portion, the top-layer sheet, the topsheet, and the absorber are compressed thickness-wise.

3. The absorbent article according to claim 2, wherein non-joined regions are respectively provided at widthwise ends of the top-layer sheet, the non-joined regions being not joined with the topsheet, and
the length between a first end of the top-layer sheet and a second end of the lengthwise compressing portion is longer than a widthwise length of the non-joined region, the first end being positioned at the lengthwise compressing portion side of the top-layer sheet and the second end being positioned at the widthwise outer side of the lengthwise compressing portion.

4. The absorbent article according to claim 3, wherein the absorber and the topsheet are not joined in at least the lower side of the non-joined region.

5. The absorbent article according to claim 2, wherein non-joined regions are respectively provided at widthwise ends of the top-layer sheet, the non-joined regions being not joined with the topsheet, and
the absorber and the topsheet are not joined in at least the lower side of the non-joined region.

6. The absorbent article according to claim 2, wherein the top-layer compressing portion is arranged in a lattice.

7. The absorbent article according to claim 1, wherein non-joined regions are respectively provided at widthwise ends of the top-layer sheet, the non-joined regions being not joined with the topsheet, and
the length between a first end of the top-layer sheet and a second end of the lengthwise compressing portion is longer than a widthwise length of the non-joined region, the first end being positioned at the lengthwise compressing portion side of the top-layer sheet and the second end being positioned at the widthwise outer side of the lengthwise compressing portion.

8. The absorbent article according to claim 7, wherein non-joined regions are respectively provided at widthwise ends of the top-layer sheet, the non-joined regions being not joined with the topsheet, and
the absorber and the topsheet are not joined in at least the lower side of the non-joined region.

9. The absorbent article according to claim 1, wherein non-joined regions are respectively provided at widthwise ends of the top-layer sheet, the non-joined regions being not joined with the topsheet, and
the absorber and the topsheet are not joined in at least the lower side of the non-joined region.

10. The absorbent article according to claim 1, wherein the top-layer compressing portion is arranged in a lattice.

11. The absorbent article according to claim 1, wherein the topsheet and the top-layer sheet are joined with an adhesive, and
the adhesive extends lengthwise, and is arranged in a plurality of columns provided by leaving an interval widthwise.

12. An absorbent article, comprising: a liquid-permeable topsheet, a liquid-impermeable backsheet, and an absorber arranged between the topsheet and the backsheet, wherein
- a liquid-permeable top-layer sheet is provided at the skin contact surface side of the topsheet,
- the top-layer sheet is arranged along a lengthwise direction of the absorbent article at a widthwise central portion of the absorbent article, and has a central region including an excretion-portion contact region configured to be arranged opposite an excretion portion of a wearer in use,
- a top-layer compressing portion in which the topsheet and the top-layer sheet are compressed thickness-wise, and an absorber compressing portion in which at least the topsheet and the absorber are compressed thickness-wise are formed in the absorbent article,
- the absorber compressing portion has a lengthwise compressing portion along the lengthwise direction of the absorbent article outboard of the top-layer sheet in the widthwise direction,
- the absorber compressing portion has a plurality of punctate compressing portions in the shape of dots that are formed intermittently outboard of the central region in the lengthwise direction, and in the punctate compressing portions, the top-layer sheet, the topsheet, and the absorber are compressed thickness-wise, and the fiber density of the topsheet is configured to be higher than the fiber density of the top-layer sheet.

13. The absorbent article according to claim 12, wherein the absorber compressing portion has a widthwise compressing portion extending in a widthwise direction outboard of the central region in the lengthwise direction, and in the widthwise compressing portion, the top-layer sheet, the topsheet, and the absorber are compressed thickness-wise.

14. The absorbent article according to claim 13, wherein non-joined regions are respectively provided at widthwise ends of the top-layer sheet, the non-joined regions being not joined with the topsheet, and
- the length between a first end of the top-layer sheet and a second end of the lengthwise compressing portion is longer than a widthwise length of the non-joined region, the first end being positioned at the lengthwise compressing portion side of the top-layer sheet and the second end being positioned at the widthwise outer side of the lengthwise compressing portion.

15. The absorbent article according to claim 13, wherein non-joined regions are respectively provided at widthwise ends of the top-layer sheet, the non-joined regions being not joined with the topsheet, and
- the absorber and the topsheet are not joined in at least the lower side of the non-joined region.

16. The absorbent article according to claim 12, wherein non-joined regions are respectively provided at widthwise ends of the top-layer sheet, the non-joined regions being not joined with the topsheet, and
- the length between a first end of the top-layer sheet and a second end of the lengthwise compressing portion is longer than a widthwise length of the non-joined region, the first end being positioned at the lengthwise compressing portion side of the top-layer sheet and the second end being positioned at the widthwise outer side of the lengthwise compressing portion.

17. The absorbent article according to claim 16, wherein non-joined regions are respectively provided at widthwise ends of the top-layer sheet, the non-joined regions being not joined with the topsheet, and
- the absorber and the topsheet are not joined in at least the lower side of the non-joined region.

18. The absorbent article according to claim 12, wherein non-joined regions are respectively provided at widthwise ends of the top-layer sheet, the non-joined regions being not joined with the topsheet, and
- the absorber and the topsheet are not joined in at least the lower side of the non-joined region.

19. The absorbent article according to claim 12, wherein the top-layer compressing portion is arranged in a lattice.

20. The absorbent article according to claim 12, wherein the topsheet and the top-layer sheet are joined with an adhesive, and
- the adhesive extends lengthwise, and is arranged in a plurality of columns provided by leaving an interval widthwise.

* * * * *